(12) United States Patent
Harrod, IV et al.

(10) Patent No.: US 10,854,340 B2
(45) Date of Patent: Dec. 1, 2020

(54) DEVICE-SIDE TESTING AND REPORTING FOR NETWORK INFRASTRUCTURE MONITORING

(71) Applicant: KONINKLIJKE PHILIPS N.V., Eindhoven (NL)

(72) Inventors: John Price Harrod, IV, North Andover, MA (US); Brian Rosnov, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/348,203

(22) PCT Filed: Nov. 8, 2017

(86) PCT No.: PCT/EP2017/078542
§ 371 (c)(1),
(2) Date: May 8, 2019

(87) PCT Pub. No.: WO2018/087116
PCT Pub. Date: May 17, 2018

(65) Prior Publication Data
US 2019/0326021 A1 Oct. 24, 2019

Related U.S. Application Data

(60) Provisional application No. 62/420,668, filed on Nov. 11, 2016.

(51) Int. Cl.
*G16H 80/00* (2018.01)
*H04L 29/08* (2006.01)
(Continued)

(52) U.S. Cl.
CPC ............. *G16H 80/00* (2018.01); *H04L 67/12* (2013.01); *H04W 8/005* (2013.01); *H04W 24/06* (2013.01); *H04W 24/10* (2013.01)

(58) Field of Classification Search
CPC ....... G16H 80/00; H04L 67/12; H04W 8/005; H04W 24/06; H04W 24/10
See application file for complete search history.

(56) References Cited

U.S. PATENT DOCUMENTS

2003/0139197 A1 7/2003 Kostic et al.
2005/0071476 A1 3/2005 Tejaswini et al.
(Continued)

FOREIGN PATENT DOCUMENTS

WO 2011103515 A1 8/2011
WO 2012093319 A1 7/2012
(Continued)

OTHER PUBLICATIONS

International Search Report and Written Opinion for International Application No. PCT/EP2017/078542, filed Nov. 8, 2017, 16 pages.

*Primary Examiner* — Wing F Chan
*Assistant Examiner* — Billy H Ng

(57) ABSTRACT

Various embodiments relate to a network device (such as a patient monitoring device) and related method and non-transitory media including one or more of the following: a wireless communication interface; patient monitoring hardware for measuring at least one physiological parameter of a patient; and a processor configured to: provide a protocol stack for enabling communication via the wireless communication interface, transmit the at least one physiological parameter via the protocol stack and the wireless communication interface, request wireless access point (AP) information about a plurality of APs from the protocol stack, generate a connectivity report based on the AP information, and transmit the connectivity report to a remote server via the protocol stack and the wireless communication interface.

9 Claims, 11 Drawing Sheets

(51) Int. Cl.
*H04W 8/00* (2009.01)
*H04W 24/06* (2009.01)
*H04W 24/10* (2009.01)

(56) References Cited

U.S. PATENT DOCUMENTS

| | | | |
|---|---|---|---|
| 2007/0064655 | A1 | 3/2007 | Ruuska |
| 2010/0110921 | A1* | 5/2010 | Famolari ............... H04W 48/17 370/252 |
| 2012/0170474 | A1* | 7/2012 | Pekarske ................ A61B 5/002 370/252 |
| 2013/0042031 | A1* | 2/2013 | Jeon ...................... H04W 48/16 710/36 |
| 2014/0105195 | A1 | 4/2014 | Balasubarmaniyan et al. |
| 2014/0313901 | A1 | 10/2014 | Yacovitch |
| 2015/0156704 | A1 | 6/2015 | Umetsu |

FOREIGN PATENT DOCUMENTS

| | | |
|---|---|---|
| WO | 2014027273 A1 | 2/2014 |
| WO | 2014207624 A2 | 12/2014 |
| WO | 2016125055 A1 | 8/2016 |

* cited by examiner

DEVICE-SIDE TESTING AND REPORTING FOR NETWORK INFRASTRUCTURE MONITORING

CROSS-REFERENCE TO PRIOR APPLICATIONS

This application is the U.S. National Phase application under 35 U.S.C. § 371 of International Application No. PCT/EP2017/078542, filed on Nov. 8, 2017, which claims the benefit of Provisional Application Ser. No. 62/420,668, filed Nov. 11, 2016. These applications are hereby incorporated by reference herein, for all purposes.

TECHNICAL FIELD

Various embodiments described herein relate to computer networks and more particularly, but not exclusively, to monitoring network infrastructures in hospitals and other medical settings.

BACKGROUND

Ease and flexibility of deployment have led to near ubiquity of wireless networks (particularly, WiFi). Compared to wired networks, however, wireless networks are susceptible to connectivity issues stemming from a variety of root causes including, for example, channel interference, low signal strength, high radio noise, coverage gaps, and client overload due to removal of physical limitations on the number of active connections. These issues can occur relatively frequently, leading to an intermittent or unstable connection that loses data intended for transmission when the connection is down. While this is an acceptable solution for most applications (e.g., web browsing, messaging, and even multimedia streaming when other measures such as client-side buffering are employed), other applications demand a much more reliable connection.

For example, in the realm of wireless patient monitoring, it is important that patient data is streamed in real time to a central device because a delay in detecting a patient episode could carry negative repercussions, and could even mean the difference between life and death. While enterprise wireless systems purport to provide tools for managing the quality of a connection throughout a hospital (or other locale in which the connection-crucial application is deployed), these systems are often closed and imperfect for the particular applications being supported. For example, such systems may attempt to organize the on-site wireless network through broad, general, and frequent networking changes that are suitable for non-time-critical applications but that server as a detriment to real-time, crucial applications.

SUMMARY

According to the foregoing, it would be desirable to provide methods and systems for performing application-specific monitoring of a wireless network infrastructure. In such networks, however, it may not be possible to define or alter the functionality of the networking hardware itself for the purposes of performing network monitoring; instead, many networks utilize off-the-shelf hardware or hardware from vendors unable to offer solutions customized in these aspects. As such, various embodiments described herein provide for client-side monitoring of network infrastructure to give an application-level view of the network and identify optimal reconfigurations in view of the specific application requirements.

Various embodiments described herein relate to a patient monitoring device including: a wireless communication interface; patient monitoring hardware for measuring at least one physiological parameter of a patient; and a processor configured to: provide a protocol stack for enabling communication via the wireless communication interface, transmit the at least one physiological parameter via the protocol stack and the wireless communication interface, request wireless access point (AP) information about a plurality of APs from the protocol stack, generate a connectivity report based on the AP information, and transmit the connectivity report to a remote server via the protocol stack and the wireless communication interface.

Various embodiments described herein relate to a method for device-side network monitoring performed by a processor of wirelessly-networked device, the method including: requesting wireless access point (AP) information about a plurality of APs from a protocol stack implemented by the processor for enabling communication via a wireless communication interface of the wirelessly-networked device, generating a connectivity report based on the AP information regarding a current state of at least one of the plurality of APs, and transmitting the connectivity report to a remote server via the protocol stack and the wireless communication interface.

Various embodiments described herein relate to a non-transitory machine-readable medium encoded with instructions for execution by a processor for device-side network monitoring performed by a processor of wirelessly-networked device, the non-transitory machine-readable medium including instructions for requesting wireless access point (AP) information about a plurality of APs from a protocol stack implemented by the processor for enabling communication via a wireless communication interface of the wirelessly-networked device, instructions for generating a connectivity report based on the AP information regarding a current state of at least one of the plurality of APs, and instructions for transmitting the connectivity report to a remote server via the protocol stack and the wireless communication interface.

Various embodiments are described wherein the processor is further configured to: identify at least one AP of the plurality of APs as a critical AP, wherein the connectivity report identifies the critical AP.

Various embodiments are described wherein in identifying the at least one AP of the plurality of APs as a critical AP, the processor is configured to perform at least one of: determining whether a connection duration for the AP surpasses a connection duration threshold, wherein processor determines the connection duration based on the requested AP information and the connection duration indicates a duration of time for which a connection has been established between the protocol stack and the AP, determining whether a roam table duration for the AP surpasses a roam table duration threshold, wherein the requested AP information includes a roam table maintained by the protocol stack and the roam table duration indicates a duration of time for which the AP has been held by the protocol stack in the roam table, and determining whether a roam table appearance count surpasses a roam table appearance count threshold, wherein the roam table appearance count indicates a number of times that the AP has been observed in the roam table over a series of executions of the step of requesting the AP information.

Various embodiments are described wherein the processor is further configured to: perform at least one test with respect to only the critical APs; and include results from the at least one test in the connectivity report.

Various embodiments are described wherein the processor is further configured to: perform at least one test with respect to the plurality of APs, wherein: the at least one test is performed in a first manner for critical APs, and the at least one test is performed in a second manner different from the first manner for APs other than critical APs; and include results from the at least one test in the connectivity report.

Various embodiments are described wherein the processor is further configured to: perform at least one test with respect to the plurality of APs; and include results from the at least one test in the connectivity report.

Various embodiments are described wherein in performing the at least one test, the processor is configured to analyze the requested AP information to determine whether an alert regarding network infrastructure should be escalated to the remote server.

Various embodiments are described wherein the at least one test includes at least one of: a test for low signal-to-noise ratio of the AP; a test for co-channel interference between APs; a test for adjacent-channel interference between APs; a test for periods spent out of network coverage of any APs; a test for low network coverage from APs; a test for a channel change in an AP; and a test for client density of an AP.

Various embodiments are described wherein the requested AP information is an 802.11 beacon of the AP and the connectivity report includes at least a portion of the information from the 802.11 beacon.

BRIEF DESCRIPTION OF THE DRAWINGS

In order to better understand various example embodiments, reference is made to the accompanying drawings, wherein.

DETAILED DESCRIPTION

The description and drawings presented herein illustrate various principles. It will be appreciated that those skilled in the art will be able to devise various arrangements that, although not explicitly described or shown herein, embody these principles and are included within the scope of this disclosure. As used herein, the term, "or," as used herein, refers to a non-exclusive or (i.e., and/or), unless otherwise indicated (e.g., "or else" or "or in the alternative"). Additionally, the various embodiments described herein are not necessarily mutually exclusive and may be combined to produce additional embodiments that incorporate the principles described herein.

Figure 1:
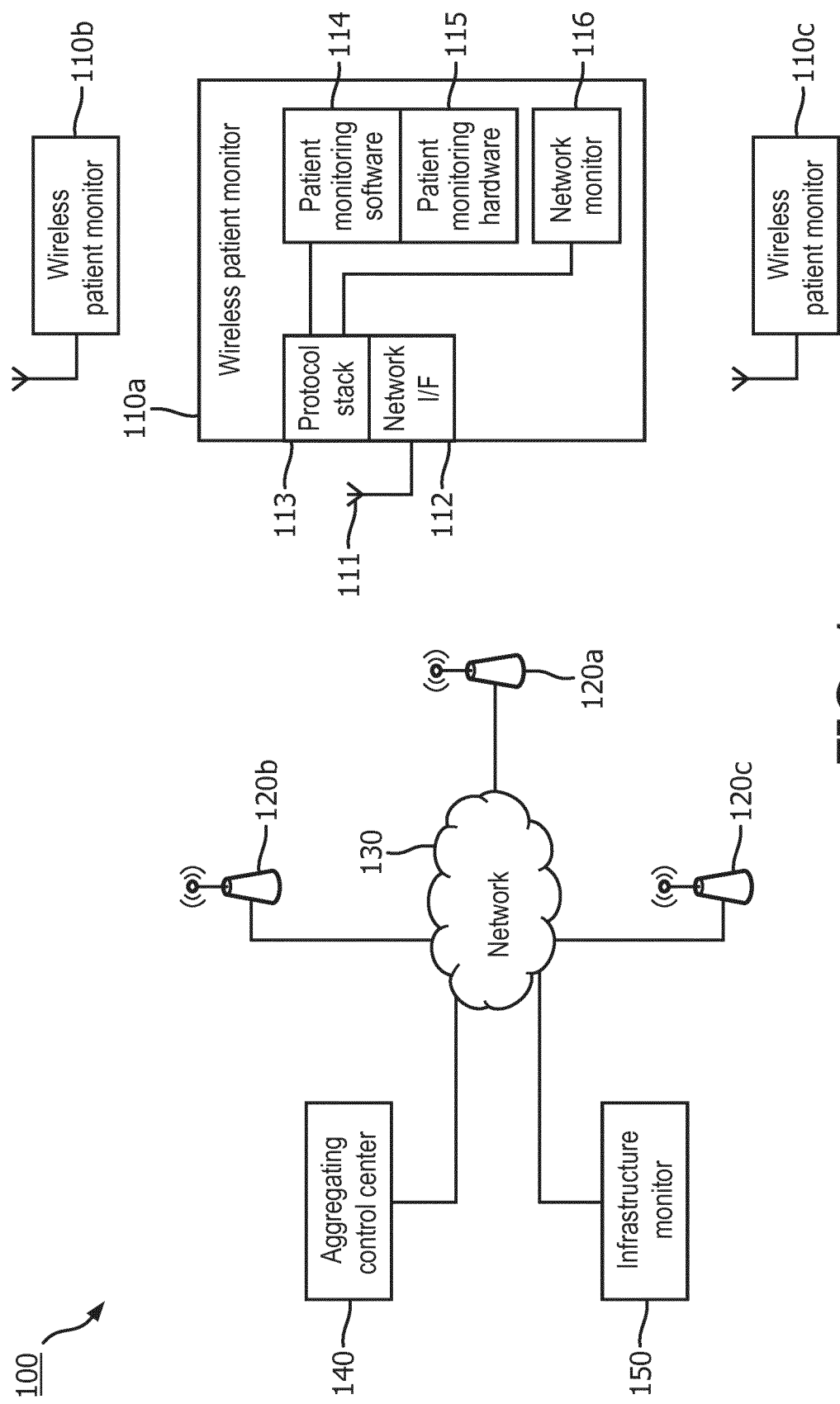
FIG. 1 illustrates an example of a network environment for providing device-side monitoring and reporting.

FIG. 1 illustrates an example of a network environment 100 for providing device-side monitoring and reporting. Network environment 100 may be deployed, at least partially, on a hospital premise, home monitoring premise, or other location where at least one application (whether clinical/medical in nature or otherwise) within the network environment 100 that would benefit from high reliability wireless communication. For example, the network environment 100 illustrates a particular embodiment of a wireless patient monitoring application. As such, the environment 100 includes one or more wireless patient monitors 110a,b,c for monitoring a physiological parameter (e.g., heart rate, blood pressure, pulse oximetry, etc.) of respective patients and reporting this information back to an aggregating control center server 140, where clinicians, nursing staff, or other staff may monitor each patient and take action as appropriate.

As shown, a wireless patient monitor 110a includes an antenna 111, network interface 112, and protocol stack 113 for enabling the wireless patient monitor 110a to transmit information wirelessly to one or more wireless access points 120a,b,c. The network interface 112 may include various hardware for transmitting and receiving digital information via an antenna on a selected frequency (or range thereof). The protocol stack 113 may include various software (executing on hardware, such as a processor) for controlling the network interface 112, including providing information for transmission and interpreting received information. While some such information to be transmitted may be "payload" information received from other components 114-116 of the wireless patient monitor 110a, other such information may include "protocol overhead" such as header and framing data. As such, the protocol stack 113 may implement various standard protocols for communicating on a wireless medium. For example, in some embodiments, the protocol stack 113 may implement one or more versions of IEEE 802.11, Internet Protocol (IP), Transmission Control Protocol (TCP), and/or User Datagram Protocol (UDP). In implementing IEEE 802.11 (or other protocols), the protocol stack 113 may include software for performing various functions such as access point 120a,b,c discovery, authentication, encryption, channel selection and communication thereof to the network interface 112, etc. The protocol stack 113 may also include various software tools for tracking network statistics (e.g., by controlling the network interface 112) such as signal strength, access point latency, number of retries attempted, number of failed transmissions, operating channel (or frequencies), etc. To support these functions (e.g., by keeping track of discovered APs and their statistics) the protocol stack 113 may maintain a roam table for storing or organizing this information. While the term "roam table" is used herein, the roam table may not actually be organized as a table and may take the form of one or more other data structures. Thus, as used herein, the term "roam table" will be understood to refer to any set of data kept by the protocol stack regarding wireless access points.

As shown, the wireless patient monitor 110a also includes patient monitoring software 114 and patient monitoring hardware 115 for monitoring and reporting various information about the patient to another device, such as the aggregating control center 140. For example, where the wireless patient monitor is adapted to report the heart rate of a patient, the patient monitoring hardware 115 may include an LED casting light on the skin of the patient and a photodiode for generating a signal based on reflected light from the LED. This signal may then be further processed by the patient monitoring hardware 115 (e.g. by one or more application-specific integrated-circuits) or by the patient monitoring software 114 to derive a photoplethysmogram (PPG) signal, from which a pulse may be extracted. The patient monitoring software 114 may then continuously, periodically, on demand, in response to a threshold crossing by the pulse, or at other times transmit the pulse values to the aggregating control center 140 by passing the information to the protocol stack 113 with an identification of the destination device. It will be understood that this is just one example of how to obtain a pulse and pulse is just one example of a patient parameter that could be communicated in the network environment. Various additional or alternative patient monitoring hardware 115 or patient monitoring software 114 will be apparent. In some embodiments, the information to be gathered or communicated may not even be clinical/medical in nature. The patient monitoring components 114, 115 may be replaced with other components in some embodiments that provide or operate within another application that relies on the wireless connection provided via the network interface 112.

The wireless patient monitor 110a includes a network monitor 116, which may include software or hardware adapted to perform high layer (e.g., application layer) monitoring of the wireless connection(s) available to the wireless patient monitor 110a. For example, in some embodiments, while the protocol stack 113 may perform some management of the connections to select an appropriate connection, such approach may not be fully suitable for some applications (e.g., applications requiring high network availability). As such, the network monitor 116 may communicate with the protocol stack 113 to gather information about the discovered access points, perform one or more tests to generate additional network statistic information or draw conclusions regarding the suitability of the network, and transmit such findings as a "connectivity report" via the protocol stack 113 to an infrastructure monitor 150. Various examples of such tests and conclusions will be described in greater detail below. As will be appreciated, while one wireless patient monitor 110a may be able to gather only limited information about the entire environment 100 (e.g., information about those access points 120a,b,c within range of the monitor 110a), a plurality of wireless patient monitors 110b performing the same or similar client-side monitoring throughout the environment 100 may be able to gather a more full picture of the network in a distributed manner.

The access points 120a,b,c may be one or more access points that communicate according to the wireless protocol implemented by the protocol stack 113, thereby providing wireless access to a wider network 130. The network 130 may include any network (or portion thereof) for communicating data such as a local area network (e.g., of a hospital or cloud computing environment), a carrier network, or the Internet. The aggregating control center 140 and infrastructure monitor 150 therefore may each be located on site with the patient monitors 110a,b,c (e.g., at a nurse's station or in the IT office of a hospital) or at a site remote therefrom such as a separate service location, home monitoring control center, or a cloud computing data center. The aggregating control center 140 and infrastructure monitor 150 may therefore be implemented in various ways such as on a server, blade, or virtual machine running on hardware in a cloud computing architecture.

The infrastructure monitor 150 may gather connectivity reports from one or more wireless patient monitor 110a and perform various network monitoring functionality based thereon. For example, in come embodiments, the infrastructure monitor may identify overloaded access points 120a,b,c or areas of the hospital or other location that suffer from low or no connectivity. In some embodiments, the infrastructure monitor 150 may implement or recommend (e.g., to a network administrator) changes to the network such as changing the operating channel of one or more access points 120a,b,c to address interference reported by the monitors 110a,b,c. As such, in various embodiments, the access points 120a,b,c may be remotely configurable by, e.g., a software-defined networking (SDN) controller. In some embodiments, the infrastructure monitor 150 may implement or communicate with an SDN controller to effect such changes. In some embodiments, the access points 120a,b,c, and infrastructure monitor 150 may belong to a closed or proprietary system wherein proprietary protocols are used for the infrastructure monitor 150 to configure various aspects of the APs 120a,b,c In some embodiments wherein the infrastructure monitor 150 provides a reporting interface to a human network administrator, the infrastructure monitor 150 may analyze connectivity reports to determine whether any alerts should be raised to the administrator.

Figure 2:
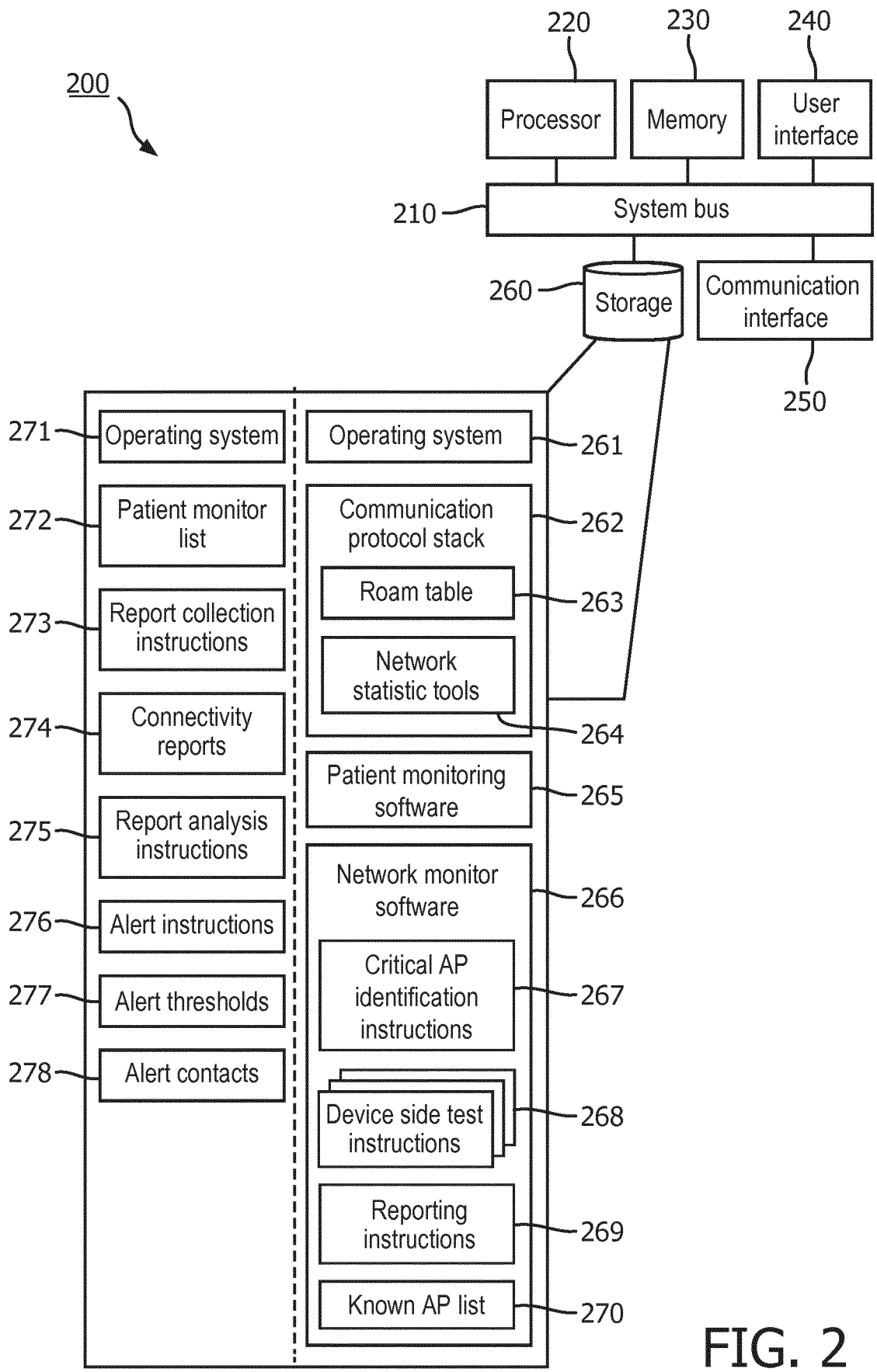
FIG. 2 illustrates an example of a hardware system for implementing a patient monitor device or an infrastructure monitor server.

FIG. 2 illustrates an example of a hardware system 200 for implementing a patient monitor device (e.g. the patient monitoring devices 110a,b,c of FIG. 1, including one or more of elements 261-270) or an infrastructure monitor server (e.g., the infrastructure monitoring server 150 of FIG. 1, including one or more of elements 271-278). As shown, the device 200 includes a processor 220, memory 230, user interface 240, network interface 250, and storage 260 interconnected via one or more system buses 210. It will be understood that FIG. 2 constitutes, in some respects, an abstraction and that the actual organization of the components of the device 200 may be more complex than illustrated. Further, while this example described various features as being implemented by a smart device and others by a server, it will be understood that this is merely an example embodiment. As noted above, the various functions may be distributed among one or more devices in many different arrangements; modifications to the software and storage 260 contents to enable such alternative arrangements will be apparent.

The processor 220 may be any hardware device capable of executing instructions stored in memory 230 or storage 260 or otherwise processing data. As such, the processor may include a microprocessor, field programmable gate array (FPGA), application-specific integrated circuit (ASIC), or other similar devices. It will be apparent that, in embodiments where the processor includes one or more ASICs (or other processing devices) that implement one or more of the functions described herein in hardware, the software described as corresponding to such functionality in other embodiments may be omitted.

The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices.

The user interface 240 may include one or more devices for enabling communication with a user such as an administrator. For example, the user interface 240 may include a display, a mouse, touchscreen, or a keyboard for receiving user commands. In some embodiments, the user interface 240 may include a command line interface or graphical user interface that may be presented to a remote terminal via the communication interface 250. In some embodiments, such has those wherein the hardware 200 implements a wireless patient monitor, the user interface 240 includes one or more sensors or other hardware for monitoring one or more physiological parameters of the patient. For example, the user interface may include an accelerometer, LED, photodiode, temperature sensor, or other hardware useful for monitoring patient physiological parameters.

The communication interface 250 may include one or more devices for enabling communication with other hardware devices. For example, the communication interface 250 may include a wired or wireless network interface card (NIC) configured to communicate with other devices. Additionally or alternatively, the communication interface 250 may include hardware for communication with nearby devices such as hardware for communication according to NFC, Bluetooth, Wi-Fi or other local wireless or wired protocols. Various alternative or additional hardware or configurations for the communication interface 250 will be apparent.

The storage 260 may include one or more machine-readable storage media such as read-only memory (ROM), random-access memory (RAM), magnetic disk storage media, optical storage media, flash-memory devices, or similar storage media. In various embodiments, the storage 260 may store instructions for execution by the processor 220 or data upon with the processor 220 may operate.

For example, where the hardware 200 implements a patient monitoring device, the storage may include an operating system 261 for coordinating the basic functionality of the device 200 and a protocol stack 262 for enabling communication via the communication interface 250 according to one or more protocols. For example, the stack 262 may implement a TCP/IP/WiFi stack for communication. In some embodiments, the stack 262 may be implemented as part of the operating system 261. In some embodiments, the stack 262 includes a roam table 263 for collecting information about discovered access points and one or more network statistics tools for testing the state of the access points or other network hardware. The storage 160 may also include patient monitoring software 265 for interpreting information provided by the sensors in the user interface 240 and reporting to an aggregation control center via the protocol stack 262.

The storage 260 also includes network monitor software 266, separate from the protocol stack 262, to perform client-side monitoring and transmit connectivity reports for use by an infrastructure monitor. As such, the network monitor software may include critical AP identification instructions 267 for identifying which known APs are considered critical to the operation of the device (e.g., to the operation of the patient monitoring software 265), one or more sets of device side test instructions for performing various tests of the network from the point of view of the device 200, and reporting instructions 269 for transmitting connectivity reports via the protocol stack 262 to the infrastructure monitor. To facilitate these instructions, the network monitor software 266 may include a known AP list 270 for tracking information related to the known APs. Such information in the known AP list may include that in the roam table 263 but may include additional information such as information discerned by the critical AP identification instructions 267 or device side test instructions 268.

Where the hardware 200 implements an infrastructure monitor, the storage 260 may include an operating system 271 for coordinating the basic functionality of the device 200. Additionally, a patient monitor list 272 may store an indication of patient monitors from which connectivity reports 274 may be received via the report collection instructions 273, e.g., in a PUSH or PULL method. Report analysis instructions 275 may analyze the received reports 274 by deriving additional statistics and generating visualizations for network administrators. If any alert thresholds 277 are crossed (e.g., minimum acceptable downtime for any single device's communication link, maximum number of devices connected to a single AP, signal strength of a critical AP falling below a minimum threshold, etc.), push alerts to one or more alert contacts 278 (e.g., network administrators) according to alert instructions 276 (e.g., via text, email, or a web portal upon next access by the contact).

It will be apparent that various information described as stored in the storage 260 may be additionally or alternatively stored in the memory 230. In this respect, the memory 230 may also be considered to constitute a "storage device" and the storage 260 may be considered a "memory." Various other arrangements will be apparent. Further, the memory 230 and storage 260 may both be considered to be "non-transitory machine-readable media." As used herein, the term "non-transitory" will be understood to exclude transitory signals but to include all forms of storage, including both volatile and non-volatile memories.

While the host device 200 is shown as including one of each described component, the various components may be duplicated in various embodiments. For example, the processor 220 may include multiple microprocessors that are configured to independently execute the methods described herein or are configured to perform steps or subroutines of the methods described herein such that the multiple processors cooperate to achieve the functionality described herein. Further, where the device 200 is implemented in a cloud computing system, the various hardware components may belong to separate physical systems. For example, the processor 220 may include a first processor in a first server and a second processor in a second server.

Figures 3, 4:
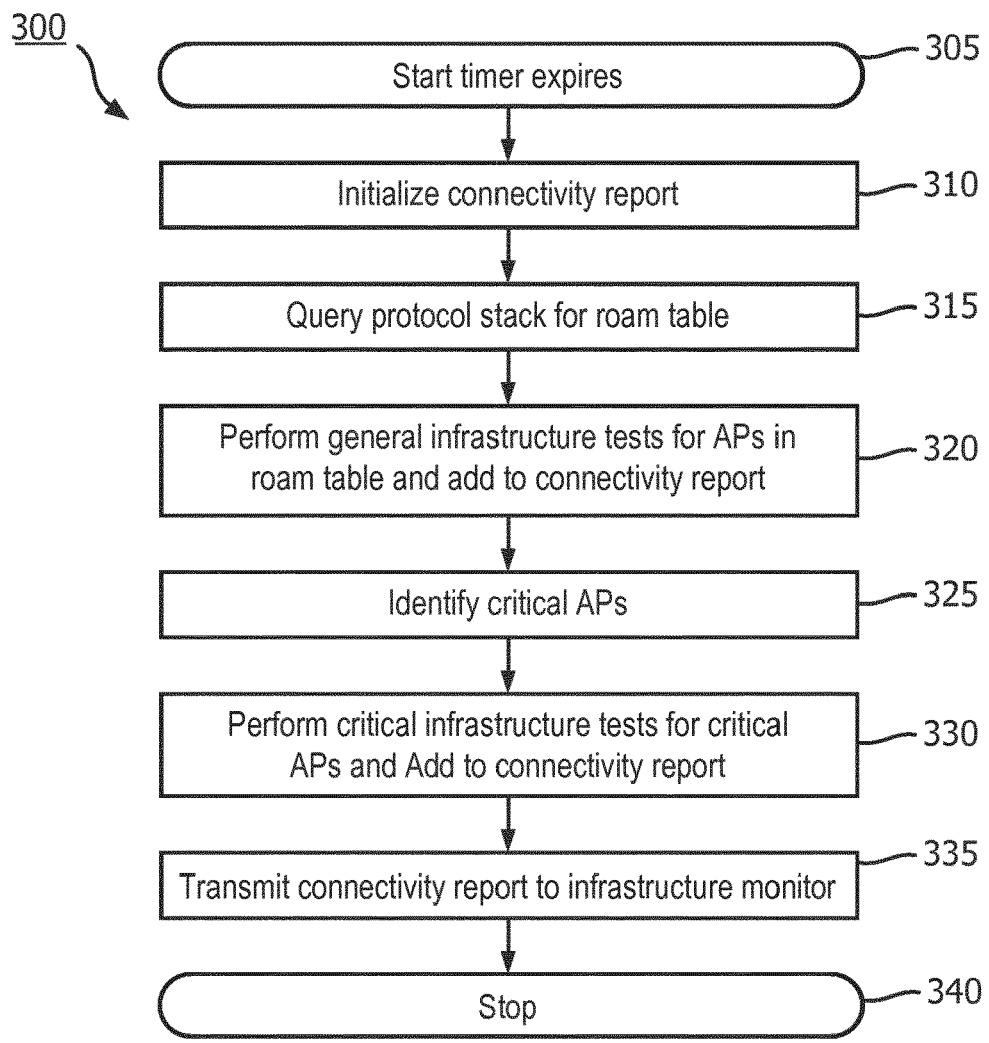
FIG. 3 illustrates an example of a method for performing device-side monitoring and reporting.
FIG. 4 illustrates an example of a known access point (AP) list.

FIG. 3 illustrates an example of a method 300 for performing device-side monitoring and reporting. The method may be performed by a device deployed within a network environment such as one or more of the wireless patient monitors 110a,b,c of FIG. 1. The method may correspond to the network monitor software 266 of FIG. 2. It will be apparent that the method is one example of a method for performing monitoring and reporting according to the principles disclosed herein and that alternative methods may be used. For example, some steps may be executed in a different order than shown, in parallel to each other, as part of separate methods (e.g., a first method for testing including steps 315-330 may be performed periodically while a second method for reporting including steps 310 and 355 may be performed upon request by an infrastructure monitor. Further, alternative or additional steps may be included in other embodiments.

In the example shown, the method 300 executes on a periodic basis and, as such, the method 300 begins in step 305 upon expiration of a periodic timer. Other triggers for beginning the method 300 (e.g., receiving a request from another device or receiving new information from the protocol stack) will be apparent. The method proceeds to step 310 where the device initializes a connectivity report. For example, in some embodiments, the method may create a new data structure or otherwise allocate memory for storing a group of information regarding access points to be reported to an infrastructure monitor. Next, in step 315, the device queries its protocol stack for information that it has gathered. For example, in various embodiments, the protocol stack (or individual layers thereof) may implement an application programmer interface (API) for requesting and receiving various information such as the contents of the roam table (including connection or link statistics). In some embodiments, step 315 may include instructing the protocol stack (e.g., via an API) to perform one or more tests using tools implemented therein (e.g. network statistics tools 264) and return the results for further analysis. In some embodiments, one or more desired pieces of information may not be accessible via an API of the protocol stack and step 315 may utilize other methods for obtaining the roam table data. For example, in some embodiments, the step 315 may directly access a portion of memory allocated to the protocol stack and read the information based on a predefined indication of the arrangement of the protocol stack's arrangement or by performing analysis to identify the location of the information (e.g., scanning for known markers of the beginning and end of the roam table, searching for a known AP name to locate the general area of the table, or applying a trained model (e.g., a classifier or other machine-learning technique) to analyze them memory and point out the network statistics. In some embodiments, step 315 may additionally include updating a known AP list based on the new information. An example of a known AP list will be described in greater detail below with respect to FIG. 4 and an example of a method for updating a known AP list will be described in greater detail below with respect to FIG. 5.

Once the roam table is obtained, the method proceeds to step 320 where the device performs general infrastructure tests on the APs in the roam table. Such tests may include analyzing the information already available regarding the APs in the roam table utilizing additional tools to communicate with other components (e.g., the APs, other devices such as wireless patient monitors, or the protocol stack) to obtain additional information not already available in the roam table. Various examples of general infrastructure tests will be described in greater detail below with respect to FIGS. 7-10.

In step 325, the device may identify which known APs are considered "critical" to the operation of the applications supported by the device. For example, a critical AP may be an AP to which the device spends a large amount of time connected or without which the device would not have an alternative access point in at least one visited area. An example of a method for identifying critical APs will be described in greater detail with respect to FIG. 6. The information of which APs are considered critical by client devices may be useful for an infrastructure monitor to take into account when considering the state and potential changes to the network. In step 330, more intensive or otherwise additional tests may be performed with respect to such critical APs (rather than all APs known) for inclusion of additional information in the connectivity report. An example of such a critical infrastructure test will be described with respect to FIG. 11.

Figure 9:
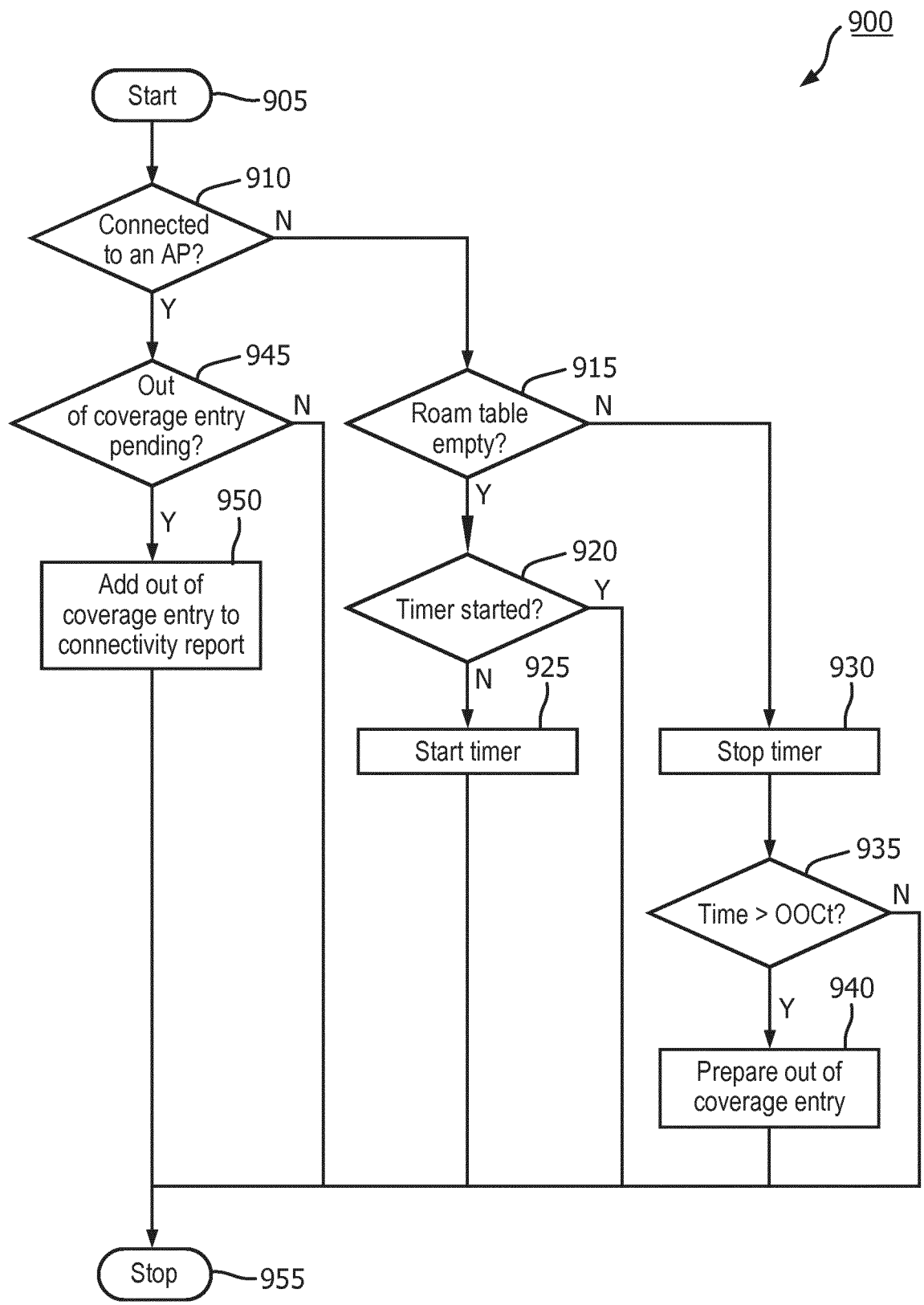
FIG. 9 illustrates an example of a method for tracking for out-of-coverage instances.
Figure 10:
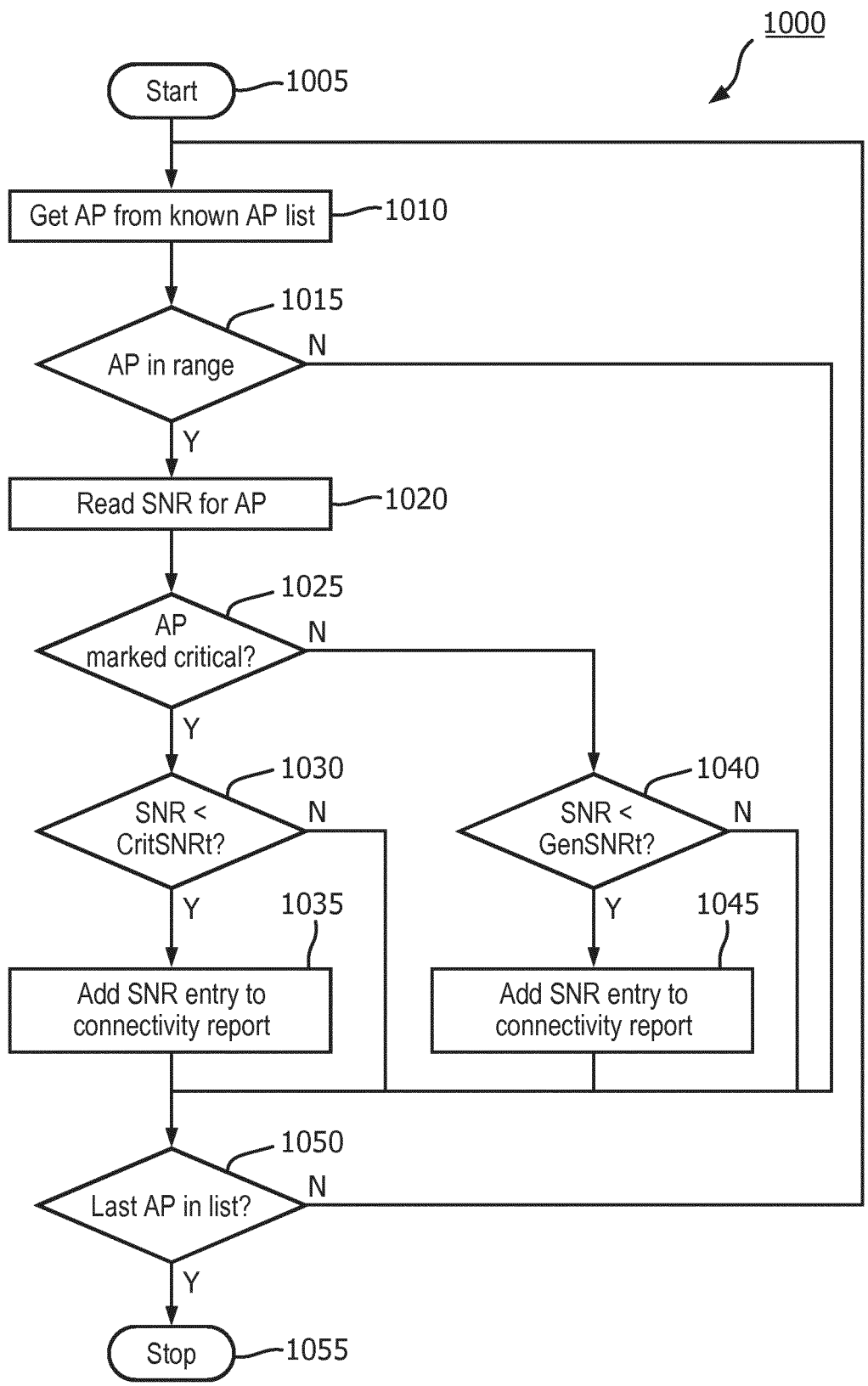
FIG. 10 illustrates an example of a method for testing for low signal-to-noise ratio (SNR)
Figure 11:
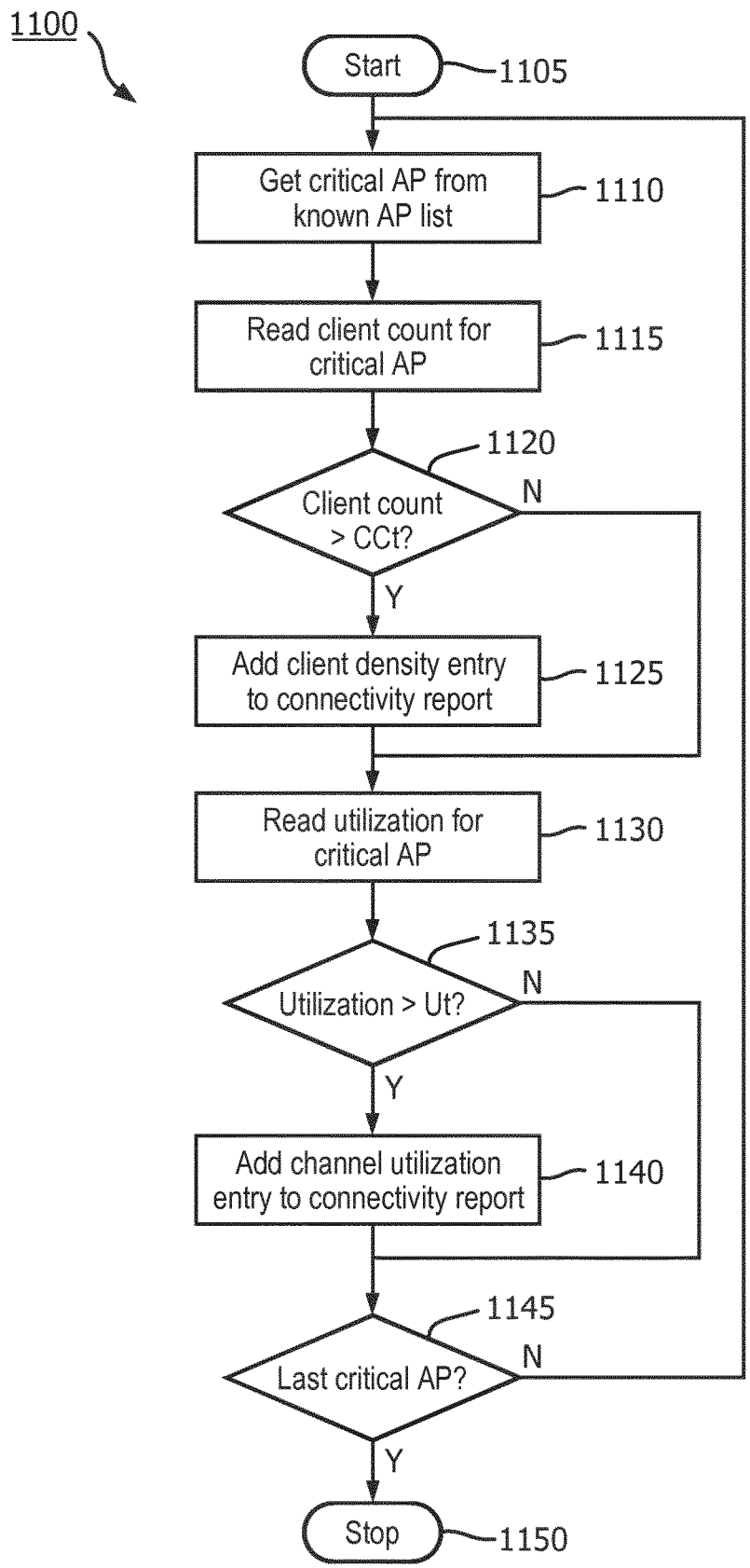
FIG. 11 illustrates an example of a method for testing for high client density on critical APs.

Various modifications to the example general infrastructure tests of FIGS. 7-10 to apply only to critical APs and modifications to the example critical infrastructure test of FIG. 11 to apply to all known APs will be apparent. Further, in some embodiments, a single method may define both general and critical infrastructure tests (e.g., a method may apply different alert or other thresholds for critical APs as compared to other APs). In such embodiments, steps 320, 330 may actually be the same step which may occur after critical APs are identified in step 325.

In some embodiments, one or more infrastructure test may not be performed within the method 300 and, instead, may be performed as part of a separate method (e.g., a method executed on a different periodic basis or in response to events such as loss of connectivity as such events occur). In some such embodiments, such other methods may write data directly into a currently-open connectivity report or may store the data resulting from the test in a location where it can be obtained and entered into the connectivity report when step 320 or 330 is executed.

In step 335, the device transmits the connectivity report to one or more infrastructure monitors. In some embodiments, the device may not transmit each connectivity report as it is formed and, instead, may aggregate multiple reports created according to the methods described herein and transmit them, for example, on demand by the infrastructure monitoring device or on a slower periodic basis (e.g., hourly or daily). In some embodiments, if a connectivity report is created at a time when the device has low or no connectivity, step 335 may wait until connectivity is restored to transmit the connectivity report. The method 300 may then proceed to end in step 340.

While various methods for including information in the connectivity report will be described below, it will be apparent that various additional or alternative methods or information may be used for constructing a connectivity report. For example, in some embodiments, the network monitor may include the data from one or more 802.11 beacons in the connectivity report. For example, every visible beacon, beacons for those APs designated critical, beacons for newly connected APs, beacons for APs to which the device has just roamed, beacons to which the device has reconnected, etc. may be gathered (e.g. from the protocol stack) and inserted into the report. Such information may include supported modulation schemes, supported data rates, active regulatory domain, AP load information such as channel utilization, 802.1 n/ac/etc. capabilities (e.g., supported channel widths, greenfield mode status, short guard interval support, Block-ACK features, transit beamforming feature support, etc.), or other vendor-specific features. As further examples, connectivity reports may include information such as device state and statistics, information about multiple APs, and application connection states.

FIG. 4 illustrates an example of a known access point (AP) list 400. In various embodiments, the network monitor component of a client device may build and maintain such a known AP list 400 to support the analysis of the device view of the network and creation of connectivity reports. In some embodiments, the known AP list 400 may correspond to the known AP list 270 of FIG. 270. The known AP list 400 may be virtually any data structure such as a database, table, array, linked list, etc. As shown, the known AP list 405-440 includes multiple fields; it will be apparent that some embodiments may use additional or alternative fields for gathering information about access points.

An access point name field 405 stores an identifier for each known AP. For example, the field 405 may store an BSSID or MAC address for each AP found in the roam table. A critical field 410 may store an indication (e.g., a Boolean value) indicating whether the AP has been identified as a critical AP for the device to which the known AP list 400 belongs (e.g., by operation of a method such as the example described below with respect to FIG. 5). A connection duration field 415 may store a duration that the device has spent connected to the access point. A duration in roam table field 420 may store a duration that the AP has been resident in the protocol stack's roam table. An instances field 425 may track the number of times the AP has appeared in the protocol stack's roam table upon subsequent queries. The durations and instances may be tracked for the lifetime of the device (i.e. never reset), from the device activation, from device assignment to a patient, for a period of time (e.g., reset every hour, day, etc.), on a rolling basis (e.g., portions of the duration older than an hour or day may be subtracted from the value), etc. An SNR field 430 may store one or more signal-to-noise ratio values associated with the AP. For example, such values may include a current or most recent SNR; or an average, median, mode minimum, or maximum of SNRs observed. Again, such SNR values may apply to the lifetime of the device or other period as described above with respect to the durations values. A channel field 435 may store an indication of a channel on which the AP operates (or has previously operated). As noted, the AP list 400 may include numerous additional fields 440.

In some alternative embodiments, the AP list 400 may not include all APs discovered and, instead, only a subset of discovered APs may be listed and tracked. For example, in some embodiments, the AP list 400 may include a predefined number of entries and whenever a new AP is discovered in the roam table of the protocol stack, the record for the oldest AP, the AP with the shortest connection duration, a random non-critical AP, or other AP may be identified for removal from the AP list 400.

As an example, a first record 450 describes a critical access point "A" to which the device is not currently connected. AP A has been seen in the roam table 432 times, and has been seen consistently in the roam table for a total of 2 hours and 21 minutes. AP A has an SNR of 60, indicating a relatively strong signal. AP A also is currently operating on channel 1.

As another example, a second record 455 describes another critical AP "B" to which the device has been connected a total of 1 hour and 14 minutes. AP B has been seen in the roam table 2,380 times and has been consistently in the roam table for a total of 1 hour and 19 minutes. AP B has an SNR of 32 and is currently operating on channel 7, but has also been observed on channels 1 and 6 in the past.

A third record 460 describes AP "C," which has not been deemed critical to the present device. It will be appreciated that in deployments including multiple similar devices in an environment that another device (e.g., another patient monitor device) may deem AP C to be critical to its own operation, e.g., due to heavy use of AP C by such other device. However, for the device to which the AP list 400 belongs, the device is not currently connected to AP C. AP C has only been seen in the roam table 50 times but is not currently in the roam table. The SNR is 0 for AP C (potentially indicating that AP C is currently out of range). AP C is also shown to operate on channel 7. Given the foregoing description, the meaning of the remaining example records 465, 470, 475 should be apparent.

Figure 5:
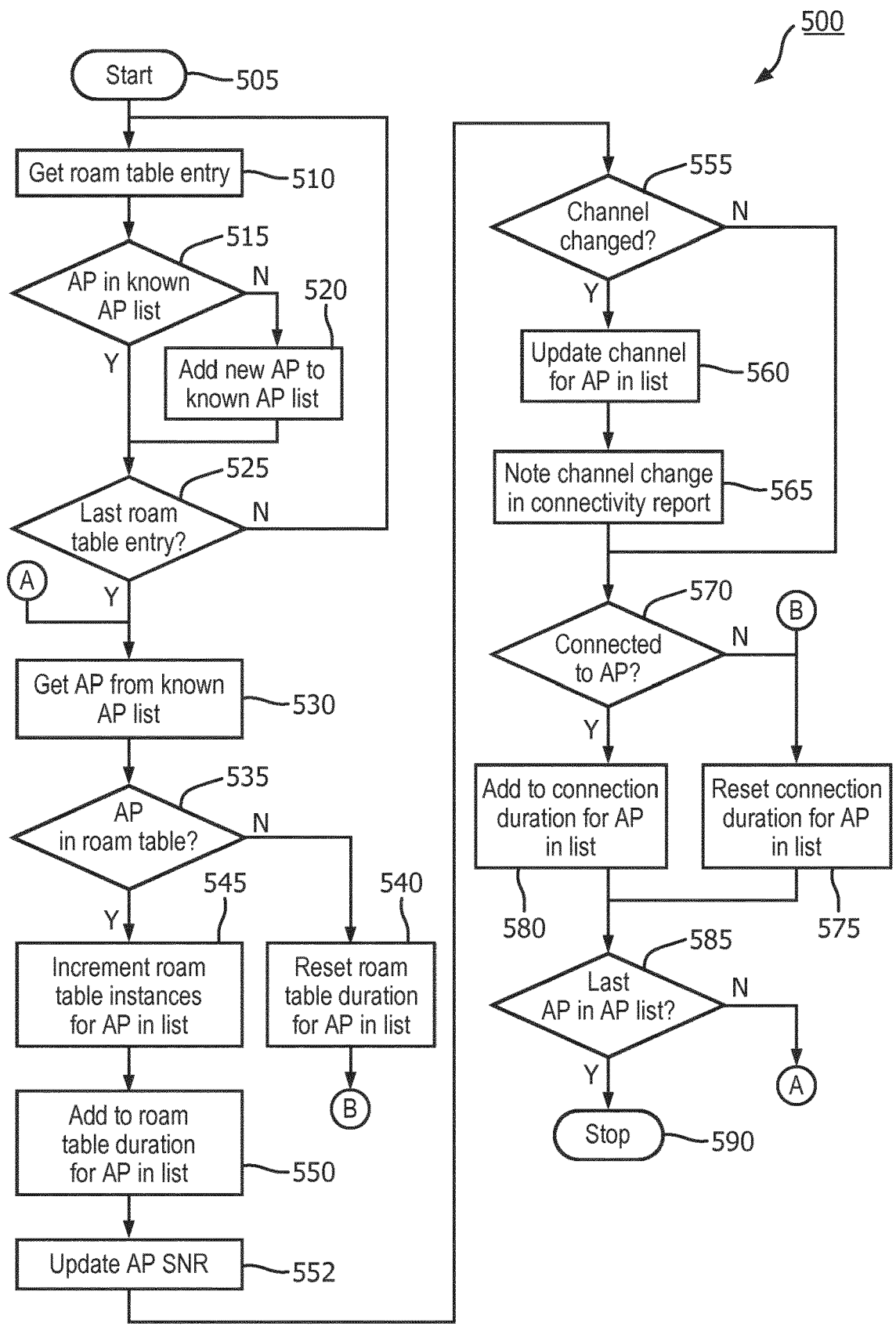
FIG. 5 illustrates an example of a method for updating a known AP list.

FIG. 5 illustrates an example of a method 500 for updating a known AP list, such as the known AP list 270 of FIG. 2 or the known AP list 400 of FIG. 4. The method 500 may be performed by a network monitor of a client device, such as the network monitor 116 of FIG. 1, and may correspond to the network monitor software 266 of FIG. 2. The method 500 may be performed (independently or as part of step 315 of FIG. 3) at various times such as periodically (e.g., every minute or every 5 minutes), on demand by another device such as an infrastructure monitor, or upon an indication from the protocol stack that the roam table has been updated.

The method 500 begins in step 505 and proceeds to step 515 where the network monitor begins updating the APs reflected in the known AP list by first retrieving a roam table entry from the protocol stack's roam table. For example, in some embodiments, the network monitor may access the roam table on a per entry basis (e.g., via an API or by directly accessing the protocol stack's memory space through identifying each successive record in the memory space). As another example, in some embodiments, the network monitor may create its own copy of the roam table and iterate through the entries of the copy. Such an approach may be useful, for example, where an API of the protocol stack is only able to provide the full roam table on request and not individual requested entries. Next, in step 515, the network monitor determines whether the known AP list already includes an entry corresponding to the AP listed in the current roam table entry. For example step 515 may include comparing the AP name of the roam table entry to each AP name in the known AP list. If there is no match, the method 500 proceeds to step 520 where the network monitor adds a new entry for the new AP in the known AP list. In embodiments wherein the known AP list has a fixed length, step 520 may also include removing an old entry (e.g., the oldest or least active entry) from the known AP list to make room for the new AP entry. In step 525, the network monitor determines whether the current roam table entry is the last one in the protocol stack's roam table. If not, the method 500 loops back to step 510 to process additional roam table entries.

Once the APs in the known AP list are updated based on the entire roam table, the method 500 proceeds to step 530 where the network monitor begins updating statistics for the known APs by first selecting an AP from the list to analyze. In step 535, the network monitor determines whether the current AP is resident in the roam table (e.g., via API, direct access to memory, etc.). If not, the network monitor resets the roam table duration and connection duration values (which may correspond to fields 420, 415 in FIG. 4, respectively) in steps 540, 575. If the AP is in the roam table currently, the method 500 instead proceeds from step 535 to step 545 where the roam table instances for the AP (which may correspond to field 425 in FIG. 4) is incremented. In step 550, the network monitor increases the roam table duration for the current AP. For example, in various embodiments, the network monitor may track the time passed between subsequent executions of the method 500 and add the time since the last execution to the current roam table duration value in the AP entry. As another example, in some embodiments such as those where the method 500 executes on a periodic basis, the network monitor may add a predetermined value to the roam table duration (e.g., a value equivalent to the period of execution of method 500). In step 552, the network device updates the AP list entry for the current AP with the current SNR (which may correspond to field 430 of FIG. 3) reported by the protocol stack.

In step 555, the network monitor determines whether the channel of the AP has changed since the last time the AP appeared in the roam table by comparing the current channel to the previously recorded channel. If so, the network monitor records the new channel of the AP in the AP list in step 560 and records an indication of the channel change in a connectivity report currently under construction or records the indication for inclusion in a connectivity report when the next connectivity report is generated (e.g., in some embodiments where the method 500 does not execute as part of method 300).

Next, the network monitor determines in step 570 whether the protocol stack and network interface are currently connected to the current AP. This information may be stored in the roam table or otherwise accessible from the protocol stack (e.g., via an API). If the device is not connected to the current AP, the method 600 proceeds to step 575. If, on the other hand, the device is connected to the current AP, then the network monitor increases the connection duration of the current AP entry (e.g., by one of the same values described above with respect to step 550). In step 585, the network monitor determines whether the current AP is the last AP in the known AP list. If not, the method loops back to step 530 to process the remaining APs in the list. Once all APs in the known AP list have been updated, the method 500 proceeds to end in step 590.

As noted above with respect to FIG. 4, various alternative or additional fields may be included in the AP list. Various modifications to the method 500 (e.g., additional, modified, or omitted steps) to support such additional fields will be apparent.

Figure 6:
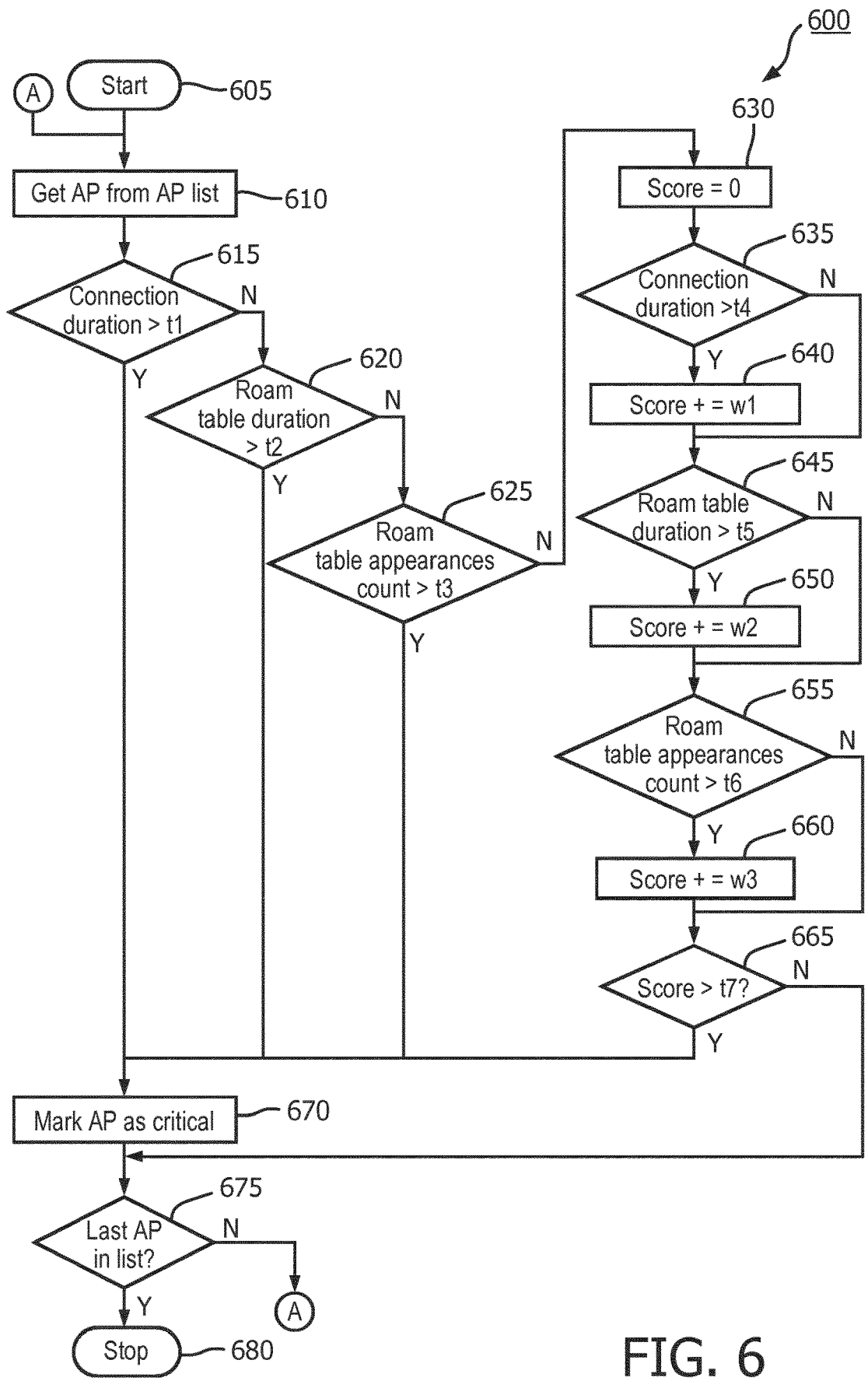
FIG. 6 illustrates an example of a method for identifying critical APs.

FIG. 6 illustrates an example of a method 600 for identifying critical APs. The method 600 may be performed by a network monitor of a client device, such as the network monitor 116 of FIG. 1, and may correspond to the critical AP identification instructions 267 of FIG. 2. The method 600 may be performed (e.g., independently or as part of step 325 of FIG. 3) at various times such as periodically (e.g., every minute or every 5 minutes), on demand by another device such as an infrastructure monitor, or upon an indication from the protocol stack that the roam table has been updated.

The method 600 begins in step 605 and proceeds to step 610 where the network device reads an AP's entry from the known AP list (e.g., the known AP list 270 or 400) for consideration. In step 615, the network monitor determines whether the connection duration stored in the entry exceeds a first connection duration threshold, t1. The first connection duration threshold t1 (and other thresholds described herein) may be predetermined or may be configurable (e.g., the infrastructure monitor may instruct each network monitor within the environment to utilize a particular threshold). As an example, t1 may be set to a value of 1 hour. If the threshold is passed, the method 600 proceeds to step 670 where the AP list entry for the current AP is marked as critical (e.g., in a field corresponding to field 410 of FIG. 4). Otherwise, the method 600 proceeds to test other metrics for judging AP criticality.

In step 620, the network monitor determines whether the roam table duration for the AP surpasses a first roam table duration threshold, t2 (e.g., 4 hours). If so, the method 600 proceeds to step 670. Otherwise, in step 625, the network monitor determines whether the roam table appearances count of the AP surpasses a first roam table appearances threshold (e.g., 1000). If so, the method proceeds to step 670. Otherwise the method 600 proceeds to step 630. Thus, any of the three statistics considered by the method 600 may alone be sufficiently high (by surpassing the appropriate threshold t1, t2, or t3) to deem the AP critical.

According to this example embodiment, even if no single value is sufficiently high, the values taken together may still justify a critical designation. In step 630, the network monitor initializes a score value to 0. Then, in step 635, the network monitor determines whether the connection duration passes a second connection duration threshold, t4, which may be smaller than the first connection duration threshold, t1. For example, t4 may be 10 minutes while t1 may be 1 hour. If so, a connection duration weight, w1, (e.g., 40) may be added to the score. As shown, the weight may be a constant, though in other embodiments, the amount added to the score may depend on the connection duration value (e.g., the amount may scale with the connection duration or the portion of the connection duration surpassing the threshold t4).

Next, in step 645, the network monitor determines whether the roam table duration passes a second roam table duration threshold, t5, which may be smaller than the first roam table duration threshold, t2. For example, t5 may be 1 hour while t2 may be 4 hours. If so, a roam table duration weight, w2, (e.g., 20) may be added to the score. As shown, the weight may be a constant, though in other embodiments, the amount added to the score may depend on the roam table duration value (e.g., the amount may scale with the roam table duration or the portion of the roam table duration surpassing the threshold t5). In step 655, the network monitor determines whether the roam table appearances value passes a second roam table appearances threshold, t6, which may be smaller than the first roam table appearances threshold, t6. For example, t5 may be 500 instances while t2 may be 1000 instances. If so, a roam table appearances weight, w3, (e.g., 20) may be added to the score. As shown, the weight may be a constant, though in other embodiments, the amount added to the score may depend on the roam table appearances value (e.g., the amount may scale with the roam table appearances or the portion of the roam table appearances surpassing the threshold t6).

Once the score has been calculated, the network monitor determines whether the score surpasses a score threshold, t7, such that the AP may be designated critical. For example, t7 may be set to a value of 50 (indicating connection duration and either roam table duration or roam table appearances must show criticality) or 70 (indicating that all three metrics must show criticality). If t7 is surpassed, the method proceeds to step 670 and then step 675. Otherwise, the method proceeds directly to step 675 where the network monitor determines whether additional APs remain for criticality assessment. If the current AP is not the last one in the list, the method 600 loops back to step 610 to analyze the remaining APs in the known AP list. Otherwise, the method proceeds to end in step 680.

As described in this example, an AP may qualify as a critical AP based solely on connection duration, roam table duration, or roam table appearances or on a combination thereof. Various alternative statistics and approaches to marking an AP as critical will be apparent. For example, in some embodiments, steps 330-365 may be omitted or one or more of steps 315-325 may be omitted. Various other modifications will be apparent.

Figure 7:
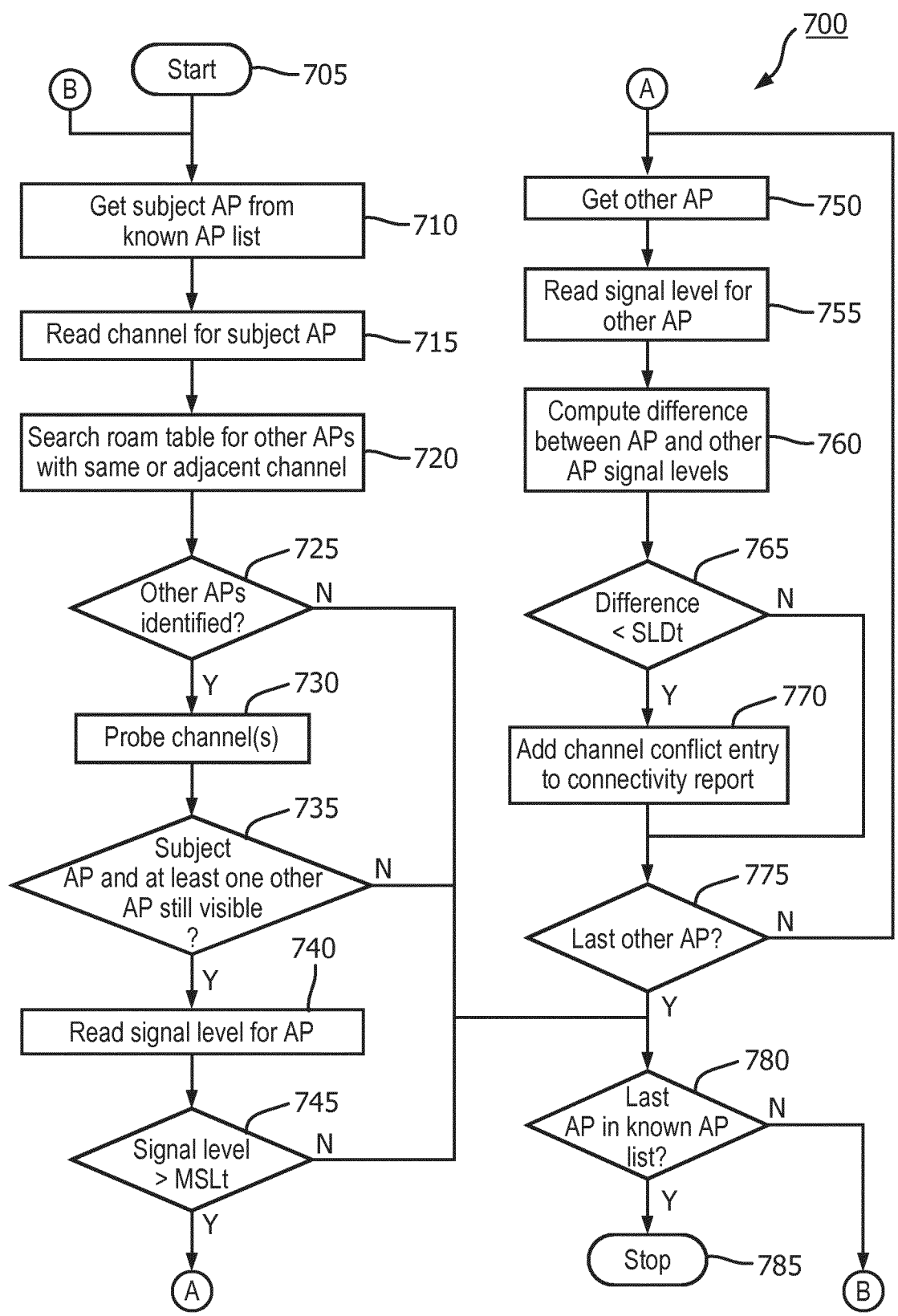
FIG. 7 illustrates an example of a method for testing for co-channel and adjacent-channel interference.

FIG. 7 illustrates an example of a method 700 for testing for co-channel and adjacent-channel interference. The method 700 may be performed by a network monitor of a client device, such as the network monitor 116 of FIG. 1, and may correspond to a one or more set of device side test instructions 268 of FIG. 2. The method 700 may be performed (e.g., independently or as part of method 300) at various times such as periodically (e.g., every minute or every 5 minutes), on demand by another device such as an infrastructure monitor, or upon an indication from the protocol stack that the roam table has been updated.

The method 700 begins in step 705 and proceeds to step 710 where the network monitor reads an AP's entry from the known AP list (e.g., the known AP list 270 or 400) for consideration. In step 715, the network monitor determines the channel associated with the current AP (e.g., by reading the channel from the retrieved AP entry). In step 720, the network monitor searches the roam table (or the known AP list in some embodiments, such as those with an unlimited or otherwise comprehensive known AP list) for any other APs that are currently on the same channel or an adjacent channel (e.g., one channel away, two channels away, etc.). In step 725, the network device determine whether any additional APs were identified in step 720. If not, the network device may determine that there is no danger of co-channel or adjacent channel interference for the current AP and the method 700 may proceed to step 780. Otherwise, if at least one other AP was identified, the method 700 proceeds to step 730. To account for potential channel changes since the last time the roam table/known AP list was updated, the network monitor may probe the channel or group of adjacent channels (e.g., by instructing the protocol stack to do so via an API) to determine whether any APs are currently visible on the channel. In step 735, the network monitor determines whether the channel probe in step 730 has revealed that either the subject AP or all of the identified other APs are no longer visible, the method 700 proceeds to step 780. Otherwise, the network monitor has identified the potential for interference and proceeds to analyze the magnitude of the problem be proceeding to step 745.

In step 745, the network device determines whether the signal level (e.g., SNR value) of the subject AP is strong enough for the present test to apply. Specifically, if the subject AP is far away and has a low signal regardless of interference, then interference may be tolerated so that the arrangement and configuration of the network APs within the environment are not overly restricted. Accordingly, in step 745, the network monitor determines whether the subject AP signal level surpasses a main signal level threshold, MSLt (e.g., 30 dB). If not, then the method 700 may proceed to step 780. Otherwise, the network proceeds to analyze the danger of interference with each identified other AP in step 750.

The network monitor retrieves one of the identified other APs in step 750 and determines the signal level of that other AP in step 755. In step 760, the network device computes a difference between the two signal levels. For example, the network device may simply subtract the other AP signal level from the subject AP signal level. In some embodiments, this step may take into account distance between the channels. For example, when the two APs are on channels that are 1 channel apart, a value (e.g., 10 or 20) may be added to the difference. Other methods for taking channel separation into account will be apparent. In step 765, the network monitor determines whether the computed difference lies below a signal level difference threshold, SLDt (e.g., 20 dB), thereby indicating an appreciable possibility or impact of channel interference. In some embodiments, different thresholds may be set for the co-channel and adjacent channel (or for each possible channel distance) interference tests. If the difference is large enough to pass the threshold, the network monitor may determine that this pair of APs does not pose a sufficient risk of interference, and the method may jump ahead to step 775. Otherwise, the network monitor adds an indication of potential channel conflict to a connectivity report (e.g., to a connectivity report presently under construction or to a spot in memory to be accessed by another process that will construct a connectivity report in the future).

In step 775, the network monitor determines whether any other APs (as identified in step 720) remain for consideration along with the current subject AP. If the current other AP is not the last to be considered, the method 700 may loop back to step 750. Otherwise, the method proceeds to step 780 where the network monitor determines whether any additional known APs remain to be analyzed as a subject AP. If the current subject AP is not the last in the known AP list, the method 700 loops back to step 710. Otherwise, the method proceeds to end in step 785.

Figure 8:
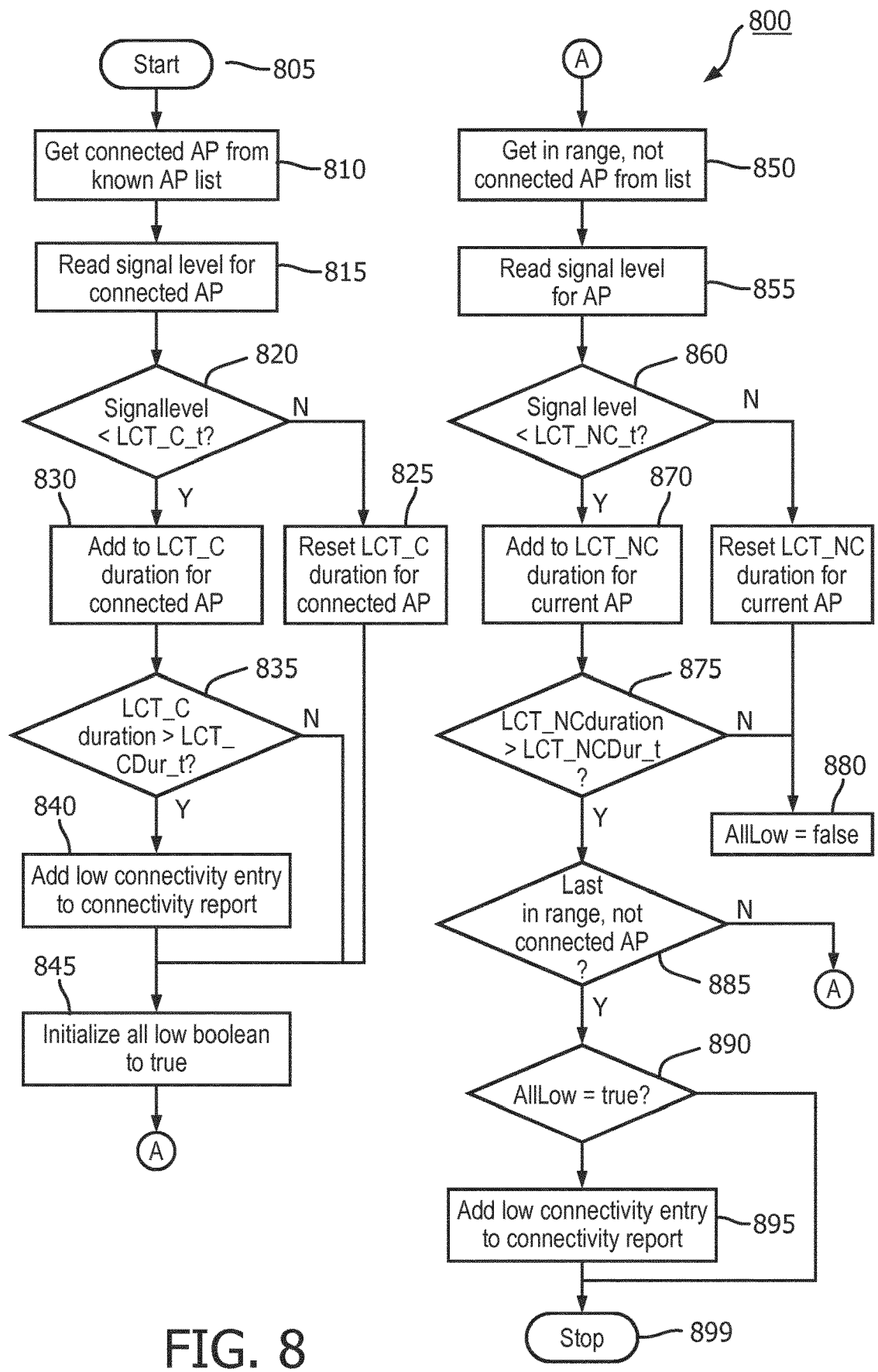
FIG. 8 illustrates an example of a method for testing for low coverage.

FIG. 8 illustrates an example of a method 800 for testing for low coverage. Low coverage may exist, for example, where the AP being used for connectivity has a relatively low signal level or where all visible APs have a relatively low signal level. The method 800, as shown, may test for both possibilities, though various modifications to test for only one of these will be apparent. The method 800 may be performed by a network monitor of a client device, such as the network monitor 116 of FIG. 1, and may correspond to a one or more set of device side test instructions 268 of FIG. 2. The method 800 may be performed (e.g., independently or as part of method 300) at various times such as periodically (e.g., every minute or every 5 minutes), on demand by another device such as an infrastructure monitor, or upon an indication from the protocol stack that the roam table has been updated.

The method 800 begins in step 805 and proceeds to step 810 where the network monitor retrieves the entry for the currently connected AP from the known AP. Next, in step 815, the network monitor reads the signal level for the connected AP from the retrieved entry. In step 820, the network monitor determines whether the connected AP has a low signal level by, for example, comparing the connected AP signal level to a "low connectivity test for connected AP threshold" (LCT_C_t) (e.g., −70 dBm). If the signal level is not low, then the network monitor will reset a "low connectivity test for connected AP duration" (LCT_C duration) that is tracked over successive executions of method 800 to zero. In other words, if the signal level is above the threshold, the connected AP is marked as having spent, as of the current execution of the method 800, 0 consecutive seconds in a low connectivity state. The method then proceeds to analyze non-connected APs in step 845.

If, on the other hand, the network monitor determines in step 820 that the connected AP does have a low signal strength currently, the method 800 proceeds to step 830 where the network monitor increases the tracked LCT_C duration based on the time since the last execution of the method 800 (e.g., by a fixed time where the method 800 is known to execute on a periodic basis or by a tracked variable that tracks the time since the last execution). In step 835, the network monitor determines whether the connected AP has had a low signal for a long enough time to justify raising a flag. This step may be performed, for example, to make sure brief or transient drops in signal strength do not raise false alarms. In some embodiments, step 835 may be omitted entirely. If the duration of low connectivity falls below a "low connectivity test connected duration threshold" (LCT_CDur_t) (e.g., 10 minutes), then the network monitor may add a low connectivity entry describing the findings to a current connectivity report (e.g., to a connectivity report under construction or to a location in memory where it can be read by another process that will construct a connectivity entry in the future). Otherwise, the method 800 skips step 840 (which may be executed on a future execution of method 800 if the LCT_C duration eventually passes the LCT_CDur_t).

The network monitor then begins to analyze non-connected APs by initializing a tracking Boolean variable, allLow, to true in step 845. Next, in step 850, the network monitor retrieves a record from the known AP list corresponding to an AP that is in range (e.g., is associated with a non-zero signal level, has a non-zero roam table duration, or is currently resident in the roam table). In step 855 the network monitor reads the signal level for the current AP from the retrieved entry. In step 860, the network monitor determines whether the current AP has a low signal level by, for example, comparing the connected AP signal level to a "low connectivity test for non-connected AP threshold" (LCT_NC_t) (e.g., −75 dBm). In some embodiments, the LCT_NC_t and LCT_C_t may be the same threshold. If the signal level is not low, then the network monitor will reset a "low connectivity test for non-connected AP duration" (LCT_NC duration) for the current AP that is tracked over successive executions of method 800 to zero. In other words, if the signal level is above the threshold, the current AP is marked as having spent, as of the current execution of the method 800, 0 consecutive seconds in a low connectivity state. The network monitor then sets the allLow variable to false in step 880, indicating that at least one non-connected AP was deemed to not have a low signal in the current execution of method 800.

If, other hand, the network monitor determines in step 860 that the current AP does have a low signal strength currently, the method 800 proceeds to step 870 where the network monitor increases the tracked LCT_NC duration based on the time since the last execution of the method 800 (e.g., by a fixed time where the method 800 is known to execute on a periodic basis or by a tracked variable that tracks the time since the last execution). In step 885, the network monitor determines whether the current AP has had a low signal for a long enough time to justify raising a flag (if the other non-connected, in range AP similarly justify a flag). This step may be performed, for example, to make sure brief or transient drops in signal strength do not raise false alarms. In some embodiments, step 875 may be omitted entirely. If the duration of low connectivity falls below a "low connectivity test non-connected duration threshold" (LCT_NC-Dur_t) (e.g., 5 minutes), then the method may proceed to step 885 (leaving allow set to true); otherwise, the method 800 may proceed to step 880. In some embodiments, LCT_NCDur_t and LCT_CDur_t may be the same threshold.

In step 885, the network monitor determines whether additional non-connected, in-range APs remain for consideration. If the current AP is not the last in-range but non-connected AP, the method 800 loops back to step 850. Otherwise, the method 800 proceeds to step 890 where the network monitor determines whether the tracking variable, allLow, has remained true during the execution of method 800. If so, then the network monitor may have determined that all in-range, non-connected APs have been in a low signal strength state for sufficiently long enough to raise a flag. The network monitor may add a low connectivity entry describing the findings to a current connectivity report (e.g., to a connectivity report under construction or to a location in memory where it can be read by another process that will construct a connectivity entry in the future) in step 895. The method 800 then proceeds to end in step 899.

FIG. 9 illustrates an example of a method 900 for tracking out-of-coverage instances. Out-of-coverage events may exist, for example, where the device enters an area where no APs (or no APs for which the device is configured to connect) are visible. The method 900 may be performed by a network monitor of a client device, such as the network monitor 116 of FIG. 1, and may correspond to a one or more set of device side test instructions 268 of FIG. 2. The method 900 may be performed (e.g., independently or as part of method 300) at various times such as periodically (e.g., every minute or every 5 minutes), on demand by another device such as an infrastructure monitor, or upon an indication from the protocol stack that the roam table has been updated.

The method 900 begins in step 905 and proceeds to step 910 where the network monitor determines whether the device is currently connected to an AP (e.g., by querying the roam table or checking the known AP list for an AP with a non-zero connected duration). If the device is not currently connected to an AP, then an out-of-coverage event may be present, and the method 900 may proceed to step 915 where the network monitor determines whether the roam table is currently empty (or, in some embodiments, only include APs to which the device cannot connect). If the roam table is empty, the network monitor may determine that an out-of-coverage event is underway. In such a case, the method 900 proceeds to step 920 where the network monitor determines whether a timer for measuring the length of the out-of-coverage event has already been started. If not, the network monitor starts a new timer in step 925 which will continue running over successive executions of method 900 until stopped by operation of another step (e.g., step 930).

If, on the other hand, the network monitor determines that the roam table is not empty in step 915, the method 900 proceeds instead to step 930 where the network monitor stops the timer (because any existing out-of-coverage event may end once the roam table is repopulated). In step 935, the network monitor determines whether the event lasted long enough to warrant raising a flag by comparing the duration tracked by the timer from start to stop to an out of coverage threshold (OOC) (e.g., 5 minutes). The event lasted long enough, the network monitor may prepare an out of coverage entry in step 940 for inclusion in a connectivity report. This entry may include various information such as the duration of the out of coverage event or GPS coordinates of the device during the event. The network monitor may not add the entry directly to the connectivity report in this step because there may not be any connection (yet) over which to send the connectivity report. In other embodiments, the network monitor may add the information directly to a connectivity report under construction, to be held until it can be transmitted.

Once the device is again connected to an AP, the method 900 proceeds from step 910 to step 945, where the network monitor determines whether one or more out of coverage entries have been constructed (e.g., by execution of step 940 on previous executions of the method 900). If so, the entry (or entries) is added to the connectivity report in step 950. The method 900 then proceeds to end in step 955.

Various modification to the method 900 will be apparent. For example, in some embodiments, the method 900 may not assume that it will execute at least one time between the time the roam table is repopulated and the time that the device is again connected to an AP. In such embodiments, steps 930-940 may be moved on duplicated to the branch of the method 900 that is visited when step 910 determines that the device is connected to an AP.

FIG. 10 illustrates an example of a method 1000 for testing for low signal-to-noise ratio (SNR). The method 1000 may be performed by a network monitor of a client device, such as the network monitor 116 of FIG. 1, and may correspond to a one or more set of device side test instructions 268 of FIG. 2. The method 1000 may be performed (e.g., independently or as part of method 300) at various times such as periodically (e.g., every minute or every 5 minutes), on demand by another device such as an infrastructure monitor, or upon an indication from the protocol stack that the roam table has been updated. As illustrated, the method 1000 may behave differently for critical APs from how it behaves for non-critical APs; as such, the method 1000 may constitute both a general infrastructure test and a critical infrastructure test. Various modifications to the other methods described herein to exhibit different behaviors for non-critical and critical APs will be apparent.

The method 1000 begins in step 1005 and proceeds to step 1010 where the network monitor retrieves an AP from the known AP list for analysis of its signal strength. In step 1015, the network monitor determines whether the AP is currently in range (e.g., by determining whether an SNR value is present or non-zero, whether the duration is non-zero, or whether the AP is currently in the roam table). If the AP is not in range, then the signal strength test may not be applied to the AP and the method 1000 may skip ahead to step 1050.

Once the network monitor finds an AP that is in range, the method 1000 proceeds to step 1020 where the network monitor reads the SNR marked for the AP in the known AP list (or from the roam table or requests a new probe) and, in step 1025 determines whether the AP is a critical AP (e.g., by reading such an indication from the current AP's entry in the known AP list). If the current AP is a critical AP, the network monitor determines whether the SNR falls below a threshold set for critical APs (CritSNRt) (e.g., 40). If the SNR is lower than the critical threshold, then the network monitor adds information describing the low SNR state to a connectivity report (e.g., directly into a connectivity report under construction or to an area in memory that will be read next time a connectivity report is created) in step 1035.

If, on the other hand, the current AP is not critical, a similar process is followed, but based on a generally applicable SNR threshold (GenSNRt) (e.g., 30). The critical threshold may be set higher than the general threshold because, for example, it may be deemed more important for critical APs to have high signal strengths compared to other known APs and therefore the bar for reporting drops in signal strength may be set higher. If, in step 1040, it is determined that the SNR falls below GenSNRt, then the network monitor adds information describing the low SNR state to a connectivity report (e.g., directly into a connectivity report under construction or to an area in memory that will be read next time a connectivity report is created) in step 1045. In step 1050, the network monitor determines whether the current AP is the last to be processed. If the current AP is not the last in the known AP list, the method 1000 loops back to step 1010 to process the remaining APs in the list. Once the entire known AP list has been considered, the method 1000 proceeds to end in step 1055.

FIG. 11 illustrates an example of a method 1100 for testing for high client density on critical APs. The method 1100 may be performed by a network monitor of a client device, such as the network monitor 116 of FIG. 1, and may correspond to a one or more set of device side test instructions 268 of FIG. 2. The method 1100 may be performed (e.g., independently or as part of method 300) at various times such as periodically (e.g., every minute or every 5 minutes), on demand by another device such as an infrastructure monitor, or upon an indication from the protocol stack that the roam table has been updated. As illustrated, the method 1100 may perform tests only on critical APs. Various modifications to the other methods described herein to apply only to critical APs will be apparent.

The method 1100 begins in step 1105 and proceeds to step 1110 where the network monitor may retrieve a first critical AP from the known AP list (if any exist). In step 1115, the network monitor may read the current count of clients connected to the current critical AP. This information may be available, for example, from the protocol stack (e.g., in the roam table, other portion of memory, or via requesting the use of one or more network tools available to the protocol stack). Alternatively, the network monitor may send a message to the critical AP to poll it directly for the information. As a further alternative, the information may be mined by the network monitor software itself from the QOS enhanced basic service set (QBSS) information element (IE) contained in the AP's beacon or probe response. In step 1120, the network monitor determines whether the client count for the critical AP is so high that it warrants reporting to the infrastructure monitor (e.g., as a potential overload of the AP) by comparing the client count to a client count threshold (CCt) (e.g., 50 clients). If the client count is sufficiently high, the network monitor adds information describing the high client density to a connectivity report (e.g., according to one or more of the previously described manners of adding to a connectivity report). Otherwise, the method 1100 skips ahead to begin a separate utilization test.

In step 1130, the network monitor reads a network utilization associated with the critical AP. Again, this may be available, for example, from the protocol stack (e.g., in the roam table, other portion of memory, or via requesting the use of one or more network tools available to the protocol stack). Alternatively, the network monitor may send a message to the critical AP to poll it directly for the information. In step 1135, the network monitor determines whether the utilization for the critical AP is so high that it warrants reporting to the infrastructure monitor (e.g., as a potential overload of the AP) by comparing the utilization to a utilization threshold (Ut) (e.g., 90%). If the utilization is sufficiently high, the network monitor adds information describing the high client density to a connectivity report (e.g., according to one or more of the previously described manners of adding to a connectivity report). Otherwise, the method 1100 skips ahead to step 1145.

In step 1145, the network device determines whether additional critical APs remain for testing. If the current critical AP is not the last in the known AP list, then the method 1100 loops back to step 1110 to process the remaining critical APs. Otherwise, the method 1100 proceeds to end in step 1150.

It will be noted that, while various embodiments described herein separate multiple tests among many separate methods, other embodiments may condense such methods into a single algorithm. For example, in some embodiments steps 845-895 and steps 1015-1045 may be inserted into method 700 (e.g. immediately after step 710) so as to leverage the loop already created by steps 710 and 780. As another example, in some embodiments, steps 1115-1140 may be inserted into method 600 (e.g., after step 670) so as to perform critical AP-specific tests immediately upon identifying a critical AP. Various other modifications of the methods described herein will be apparent.

Figure 12:
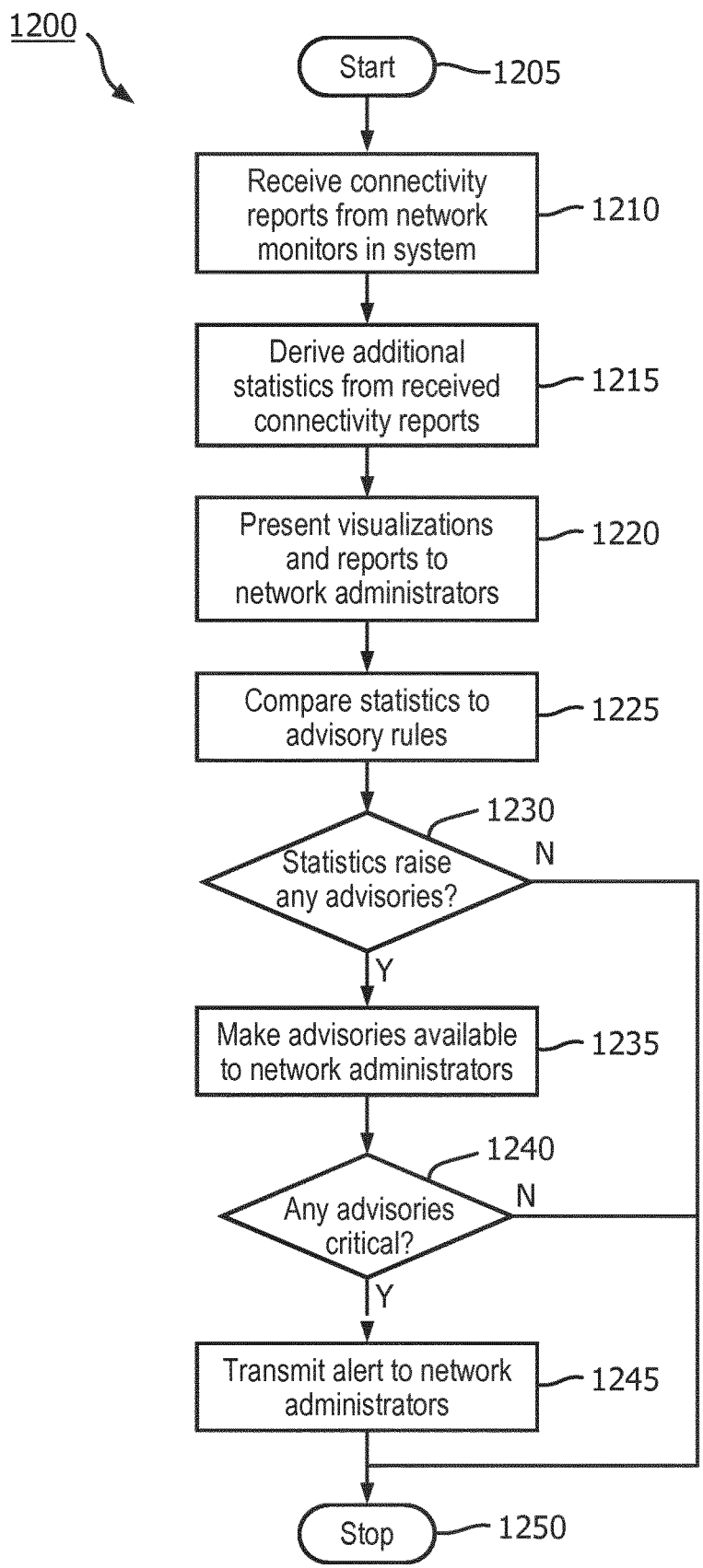
FIG. 12 illustrates an example of a method for processing connectivity reports for presentation to network administrators.

FIG. 12 illustrates an example of a method 1200 for processing connectivity reports for presentation to network administrators. The method 1200 may be performed by an infrastructure monitor (e.g., infrastructure monitor 150 of FIG. 1) and may correspond to the report collection instructions 273, report analysis instructions 275, and alert instructions 276 of FIG. 2. The method 1200 may be performed periodically (e.g., every 5 minutes, every hour, etc.), upon receiving connectivity reports (e.g. on each new connectivity report, upon receiving 5 new connectivity reports, upon receiving at least one connectivity report from each active network monitor, etc.), or on some other basis.

The method 1200 begins in step 1205 and proceeds to step 1210 where the infrastructure monitor receives one or more connectivity reports from network monitors deployed in client devices of the system. In step 1215, the infrastructure monitor derives additional statistics (e.g., various statistics discernable across multiple connectivity reports such as average AP load, a listing of all APs marked as critical, a map of out-of-coverage events, a timeline of low-connectivity events, etc.) and, in step 1220, the infrastructure monitor presents (or generates for presentation upon later request) one or more visualizations of the connectivity reports.

The infrastructure monitor then begins to determine whether any alerts should be raised by, in step 1225, comparing statistics (whether delivered in connectivity reports or derived therefrom) to one or more predefined alert rules. For example, a rule may state that an alert should be raised if an AP marked as critical by at least 10 devices (e.g., patient monitors) reaches 70% utilization. Table 1, below, includes another example of multiple advisory rules to be raised based on events reported in a connectivity report

TABLE 1

| Advisory | Level |
|---|---|
| Channel Change | Informational |
| Co-channel Interference | Warning if signal delta is >10 dBm<br>Critical if signal delta is <10 dBm |
| Adjacent channel Interference | Warning if signal delta is >5 dBm<br>Critical if signal delta is <5 dBm |
| Low-Coverage | Warning if the maximum signal level seen is <5 dBm below the minimum required signal level<br>Critical if the maximum signal level seen is >5 dBm below the minimum required signal level |
| No-Coverage | Informational |

If, in step 1230, the infrastructure monitor determines that one or more of the advisory rules have been met, then in step 1235, the infrastructure monitor makes identifications of those advisories available to the network administrators (e.g., by rendering a list of the advisories on a home page or advisory page of an admin portal/website when accessed by administrators). The infrastructure monitor then goes on to determine whether any of the advisories merit pushing a notification to one or more network administrators by determining, in step 1240, whether any of the advisories resulting from step 1225 are critical. Advisories may be deemed critical, for example, based on the associated rule being deemed critical, based on a specific critical threshold or other critical criteria being met within the rule (e.g., a rule may include a normal threshold and a critical threshold), based on the duration that that advisory has been present, based on one or more critical APs being impacted, etc. If so, the infrastructure monitor may transmit an alert (e.g., a text message, email, phone call, etc.) to the network administrators in step 1245. The method 1200 may proceed to end in step 1250.

According to the foregoing, various embodiments enable and provide for enhanced monitoring of a wireless network infrastructure for more robust availability and performance. For example, by tasking client devices of the network with performing at least some monitoring and reporting beyond that performed by standard protocols, the overall monitoring can be distributed among multiple (potentially numerous) devices, rather than one or a few central devices repeatedly probing the network to learn the network state. Further, by providing for client devices that identify critical nodes, the amount of redundant processing and reporting performed in such a distributed system can be reduced (along with the benefit of learning which APs are deemed critical itself). Various additional benefits will be apparent in view of the foregoing.

It should be apparent from the foregoing description that various example embodiments of the invention may be implemented in hardware or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:
1. A patient monitoring device comprising:
a wireless communication interface;
patient monitoring hardware for measuring at least one physiological parameter of a patient; and
a processor configured to:
provide a protocol stack for enabling communication via the wireless communication interface,
transmit the at least one physiological parameter via the protocol stack and the wireless communication interface,
request wireless access point (AP) information about a plurality of APs from the protocol stack, the AP information including connection or link statistics,
identify at least one AP of the plurality of APs as a critical AP,
perform at least one test with respect to the plurality of APs, wherein:
the at least one test is performed in a first manner for critical APs, and
the at least one test is performed in a second manner different from the first manner for APs other than critical APs; and generate a connectivity report based on the AP information, wherein the connectivity report identifies the critical APs, including results from the at least one test; and transmit the connectivity report to a remote server via the protocol stack and the wireless communication interface.

2. The patient monitoring device of claim 1, wherein in identifying the at least one AP of the plurality of APs as a critical AP, the processor is configured to perform at least one of:

determining whether a connection duration for the AP surpasses a connection duration threshold, wherein processor determines the connection duration based on the requested AP information and the connection duration indicates a duration of time for which a connection has been established between the protocol stack and the AP, determining whether a roam table duration for the AP surpasses a roam table duration threshold, wherein the requested AP information comprises a roam table maintained by the protocol stack and the roam table duration indicates a duration of time for which the AP has been held by the protocol stack in the roam table, and determining whether a roam table appearance count surpasses a roam table appearance count threshold, wherein the roam table appearance count indicates a number of times that the AP has been observed in the roam table over a series of executions of the step of requesting the AP information.

3. The patient monitoring device of claim 1, wherein in performing the at least one test, the processor is configured to analyze the requested AP information to determine whether an alert regarding network infrastructure should be escalated to the remote server.

4. The patient monitoring device of claim 1, wherein the at least one test comprises at least one of:
a test for low signal-to-noise ratio of the APs;
a test for co-channel interference between APs;
a test for adjacent-channel interference between APs;
a test for periods spent out of network coverage of any APs;
a test for low network coverage from APs;
a test for a channel change in the AP; and
a test for client density of the AP.

5. The patient monitoring device of claim 1, wherein the requested AP information is an 802.11 beacon of the AP and the connectivity report includes at least a portion of the information from the 802.11 beacon.

6. A method for device-side network monitoring performed by a processor of a wirelessly-networked device, the method comprising:

requesting wireless access point (AP) information about a plurality of APs from a protocol stack implemented by the processor for enabling communication via a wireless communication interface of the wirelessly-networked device, the AP information including connection or link statistics, identifying at least one AP of the plurality of APs as a critical AP, performing at least one test with respect to the plurality of APs, wherein:
the at least one test is performed in a first manner for critical APs, and
the at least one test is performed in a second manner different from the first manner for APs other than critical APs; and generating a connectivity report based on the AP information regarding a current state of at least one of the plurality of APs, including results from at least one test, wherein the connectivity report identifies the at least one critical AP, and transmitting the connectivity report to a remote server via the protocol stack and the wireless communication interface.

7. The method of claim 6, wherein identifying at least one AP of the plurality of APs as a critical AP comprises at least one of:

determining whether a connection duration for the AP surpasses a connection duration threshold, wherein processor determines the connection duration based on the requested AP information and the connection duration indicates a duration of time for which a connection has been established between the protocol stack and the AP, determining whether a roam table duration for the AP surpasses a roam table duration threshold, wherein the requested AP information comprises a roam table maintained by the protocol stack and the roam table duration indicates a duration of time for which the AP has been held by the protocol stack in the roam table, and determining whether a roam table appearance count surpasses a roam table appearance count threshold, wherein the roam table appearance count indicates a number of times that the AP has been observed in the roam table over a series of executions of the step of requesting the AP information.

8. The method of claim 6, wherein performing the at least one test comprises analyzing the requested AP information to determine whether an alert regarding network infrastructure should be escalated to the remote server.

9. The method of claim 6, wherein the at least one test comprises at least one of:
a test for low signal-to-noise ratio of the AP;
a test for co-channel interference between APs;
a test for adjacent-channel interference between APs;
a test for periods spent out of network coverage of any APs;
a test for low network coverage from APs;
a test for a channel change in an AP; and
a test for client density of an AP.

* * * * *